United States Patent [19]
> Ballinger

[11] Patent Number: 4,532,615
[45] Date of Patent: Jul. 30, 1985

[54] PHASED ARRAY FOR AN ULTRASONIC TRANSDUCER

[75] Inventor: Dale O. Ballinger, Lakewood, Colo.

[73] Assignee: Biosound, Inc., Indianapolis, Ind.

[21] Appl. No.: 425,805

[22] Filed: Sep. 28, 1982

[51] Int. Cl.³ .......................... G01S 7/52; G01S 15/02
[52] U.S. Cl. ........................................ 367/87; 367/99; 367/105
[58] Field of Search ................ 367/87, 99, 105, 122, 367/123, 905

[56] References Cited

U.S. PATENT DOCUMENTS

| | | | |
|---|---|---|---|
| 3,936,791 | 2/1976 | Kossof | 340/1 |
| 4,149,420 | 4/1979 | Hutchinson et al. | 73/626 |
| 4,234,937 | 11/1980 | Eggleton et al. | 367/11 |
| 4,241,611 | 12/1980 | Specht et al. | 367/105 X |
| 4,316,271 | 2/1982 | Everet | 367/140 |
| 4,344,159 | 8/1982 | Ballinger | 367/87 |

OTHER PUBLICATIONS

H. T. O'Neil; Bell Telephone Labs Report entitled "Theory of Focusing Radiators", May 21, 1949, pp. 1–11.

Primary Examiner—Richard A. Farley
Attorney, Agent, or Firm—Woodard, Weikart, Emhardt & Naughton

[57] ABSTRACT

An improved ultrasonic transducer in which signals from portions of the transducer located a distance apart from each other are compensated for the cancellation affects due to a reflected energy striking one part before the other by use of switching circuits which pass either in-phase or out-of-phase components from the portions of the transducer to a summing circuit in such a manner that the summed output is improved.

22 Claims, 10 Drawing Figures

PHASED ARRAY FOR AN ULTRASONIC TRANSDUCER

BACKGROUND OF THE INVENTION

This invention is in the field of ultrasonic devices and particularly ultrasonic devices which are used in medical practice for providing an image output of various internal structures such as the heart. Systems for performing this function may be found in, for example, co-pending application Ser. No. 173,874 filed July 30, 1980, in the name of James M. Gessert and assigned to the assignee of the present invention and in patents such as Hutchison et al. U.S. Pat. No. 4,149,420 issued Apr. 17, 1979, and Eggleton et al. U.S. Pat. No. 4,234,937 issued Nov. 18, 1980.

In such systems, ultrasonic energy is transmitted into the body by a transducer which, for example, may be pivotly mounted such as is shown in the Donald A. Everet U.S. Pat. No. 4,316,271 issued Feb. 16, 1982, and assigned to the assignee of the present invention. Echos from parts of the body are reflected to the transducer and then converted into electrical signals for use in the imaging systems. The ultrasonic transducer may comprise a piston like element which alternately acts as a transmitter and a receiver producing a pulse of ultrasonic energy and then waiting for the return echo to produce an electric signal, or maybe an array of elements such as the Linear Array Ultrasonic Transducer seen in the George Kossoff U.S. Pat. No. 3,936,791 issued Feb. 3, 1976, which is capable of producing a focused beam of ultrasonic energy. A useful alternate configuration for an array of transducers, particularly in medical field is for the elements to be annularly arranged as concentric rings about a central portion like that shown in the Specht et al. U.S. Pat. No. 4,241,611 issued Dec. 30, 1980.

A difficulty arises when an array of transducing elements is employed by virtue of the fact that the echo returning from a reflecting object produces a wave front which may strike the various elements of the array at different times. If the outputs of the elements are all summed, then at certain positions of the remote object, the delay between the time that the wave front strikes one detector and another may be approximately equal to the wavelength of the energy thus producing a cancellation effect in the summer and a consequent zero output. To overcome this problem, it is common for delay circuits to be employed connected to the various elements so that the signals received by the elements are delayed by various amounts thereby causing the cancellation effect to be overcome and the output of the summer truly additive of the signals received by each of the elements. Delay lines of this sort are shown, for example, in the above referred to U.S. Pat. No. 3,936,791. Ideally, the amount of delay should be altered for each specific distance to the object so that the summed signals remain in phase throughout the entire range of the transducer. Unfortunately, electrically alterable delay lines are difficult and expensive to manufacture and accordingly in practice the delay lines normally have tabs which are switched at appropriate times after a transmit pulse has been sent to provide for several "zones" of delay.

SUMMARY OF THE INVENTION

The present invention overcomes the problems of the use of delay lines in a phased array type of transducer by providing at the output of each of the transducing elements a differential amplifier which can produce either an in-phase or out-of-phase signal corresponding to the signal being produced by the transducing element. A plurality of switches are connected to the output of the differential amplifiers and are controlled by a timing and logic circuit which operates to pass either the in-phase or the out-of-phase component to the summing circuit. The timing and logic circuit is controlled in accordance with the time from the propogation of the transmitted pulse and thus when signals received by two transducing elements are such that they would tend to subract from one another, the phase of one of them is switched so that they add. In this manner, the summed output signal can always receive signals that are either equal to or greater than would be the case if the signals were summed without switching. Furthermore, there will be no conditions in which the signals cancel and, in fact, the output over the range of the device is improved by factors from one to ten depending upon the distance of the reflecting object. A further benefit to be obtained utilizing the present invention is that the beam width of the signal is narrowed so as to produce greater resolution than was previously obtainable.

DETAILED DESCRIPTION OF THE PREFERRED EMBODIMENT

Figure 1:
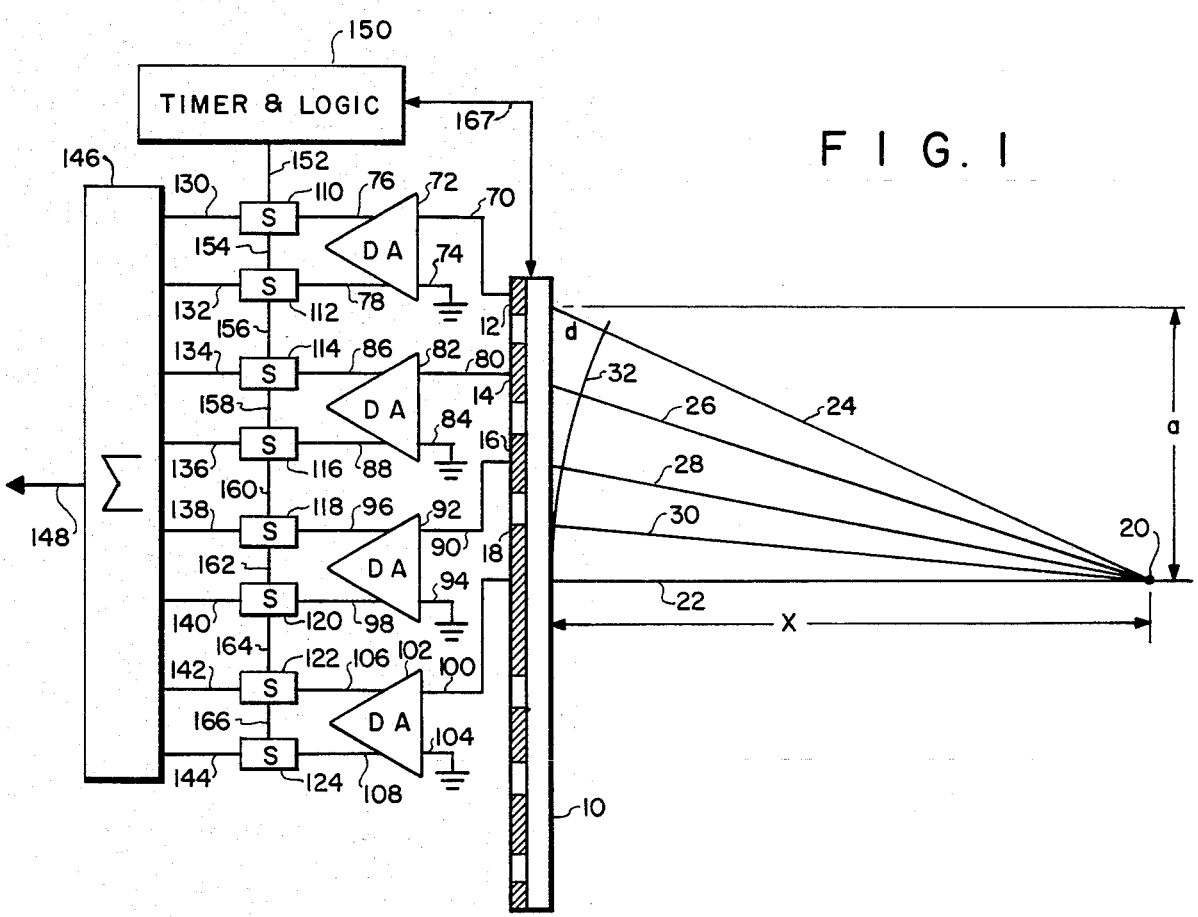
FIG. 1 is a schematic and cut away drawing of a transducer array and the circuitry of the present invention.

In FIG. 1 an ultrasonic transducer 10 is shown consisting of four concentrically arranged transducing elements 12, 14, 16, and 18. While in the preferred embodiment, it will be presumed that a concentric annular array of four elements is being utilized, it should be understood that the principals of the present invention would apply equally well to a linear array or to an array containing fewer or more than four elements or, as a matter of fact, to a single ultrasonic piston having a plurality of pick-off points. It will be noted that the cross-sectional area of element 12 is somewhat smaller than that of element 14 which in turn is somewhat smaller than that of element 16 and that element 18 is largest of all. The actual arrangement of an annular array is preferrably such that the transducing elements 12, 14, 16, and 18 all have the same area and accordingly their cross-sectional dimensions would have to decrease from the center.

The transducer 10 operates to produce a pulse of sonic energy which travels to the right in FIG. 1 where it will be reflected from a remote object such as is shown as point 20 along axis 22 of the transducer 10. It should be understood that the energy transmitted by transducer 10 may be a plane wave or may be focused as discussed, for example, in the above referred to U.S. Pat. Nos. 3,936,791 and 4,241,611. It should also be understood that all of the elements 12-18 may operate together to produce the ultrasonic pulse and then change modes so as to receive the reflected energy or, one of the elements such as the central element 18 could be used to transmit the energy while the elements 12, 14, and 16 receive the pulse echo or, the transmission of the energy could be from another transducing element entirely with the reflected energy being received by elements 12-18.

In any event, sonic energy reflected from the object at point 20 would return to the transducer 10 along the lines such as shown by reference numerals 24, 26, 28, and 30. It is obvious from FIG. 1 that the path 24 is longer than 26 which in turn is longer than path 28 and path 30 is the longest of the four. As such, it will take a longer period of time for the echo to return along path 24 than along the other paths. A circular arc 32 has been shown in FIG. 1 to show the difference in path lengths and for purposes of explanation, the difference in length between path 24 and the distance to the transducer along the axis 22 is shown in FIG. 1 to be "d". If the distance from the center of element 18 to the center of element 12 is defined as "a" and if the distance from transducer 18 along axis 22 to point 20 is defined as "x" then, $x = (a^2 - d^2)/2d$. If it is further assumed that the frequency of the ultrasonic energy is 3.5 MHz and that the speed of sound in a body is 1540 meters per second, then the wavelength of the ultrasonic energy will be 0.44 millimeters.

As explained above, cancellation of a signal between one receiving element and another occurs when the distance "d" is equal to a whole wavelength of the ultrasonic energy. Thus, when the distance "d" is equal to 0.44 millimeters, 0.88 millimeters, 1.32 millimeters, 1.76 milimeters, or 2.20 millimeters, there will be a cancellation effect. From the above equation, if it is assumed that "a" has a value of 6.5 millimeters, this will occur at distances where "x" is equal to approximately 47.79 millimeters, 23.57 millimeters, 15.34 millimeters, 11.12 millimeters, and 8.50 millimeters, respectively. At other distances from the transducer, the signals received by the elements 12, 14, 16, and 18 will variously add and subtract so as to produce final additive values other than zero.

Figure 2A:
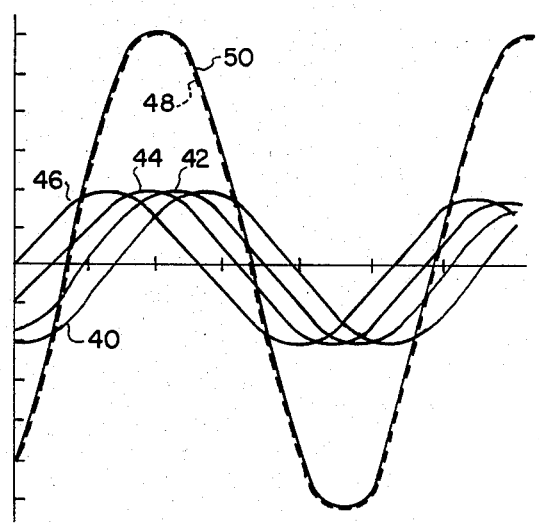
FIGS. 2a through 2f are graphs showing the signals received by the transducer elements of FIG. 1 and the output signal of the summing circuit compared with the output signal which would have existed if there were no compensation for time delay.

The additive and subtractive effects of the various ultrasonic signals received by transducing elements 12, 14, 16, and 18 can be seen by an examination of FIGS. 2a through 2f. In FIG. 2a, four curves 40, 42, 44, and 46 are shown as sine waves which are slightly displaced one from another and may represent the signals being received by transducing elements 12, 14, 16, and 18 respectively in FIG. 1. In FIG. 2a the situation is such as would occur if the object were quite remote from the transducer at say, 150 millimeters. In such a situation the value of "d" in FIG. 1 is fairly small and accordingly the distance between the four waves is likewise very small. In FIG. 2a a dashed curve 48 is shown which represents a summation of the curves 40, 42, 44, and 46 although not in scale for convenience. A second curve 50 is shown co-extensive with dash-line curve 48 and represents the relative magnitude of the summed output of the transducer elements 12, 14, 16, and 18 of FIG. 1 when the present invention is employed as will be further explained.

Figure 2B:
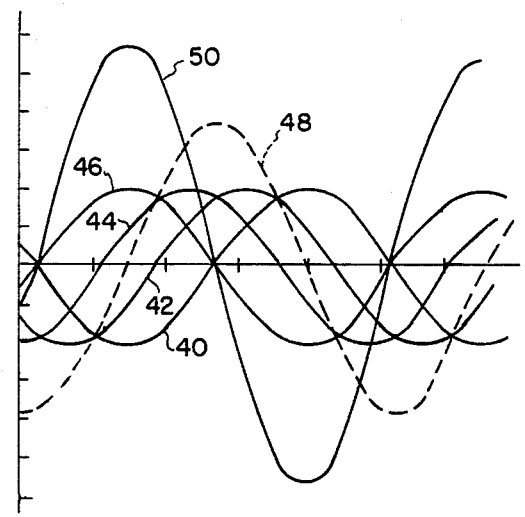

In FIG. 2b the curves 40, 42, 44, and 46 are shown when an object is located at a distance of about 80 millimeters from the transducer head. It is seen now that the distance between the various curves 40-46 has increased somewhat over what was the case in FIG. 2a and, as a result, the summation curve shown by dashline 48 is decreased in magnitude since the curves are not as well additive as they were in FIG. 2a. It will be noted that the curve 50 showing the relative magnitude when the present invention is employed is greater than the curve 48.

Figure 2C:
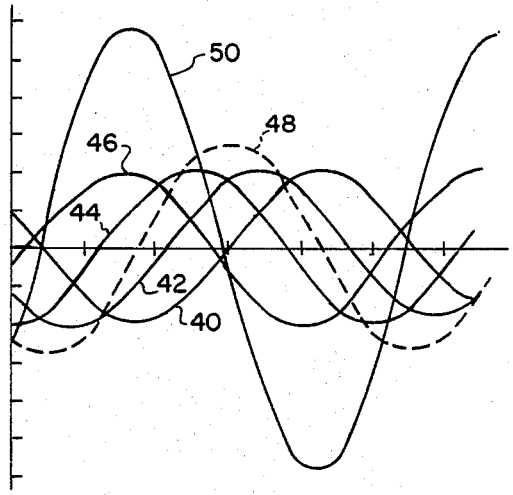

In FIG. 2c, the situation is represented where the object is located at about 70 millimeters from the transducer and it can be seen that curves 40, 42, 44, and 46 are again further apart than they were in FIGS. 2a and 2b. Likewise the summation curve 48 has further decreased and that the relative curve 50 representing the situation with the use of the present invention is significantly larger than curve 48.

Figure 2D:
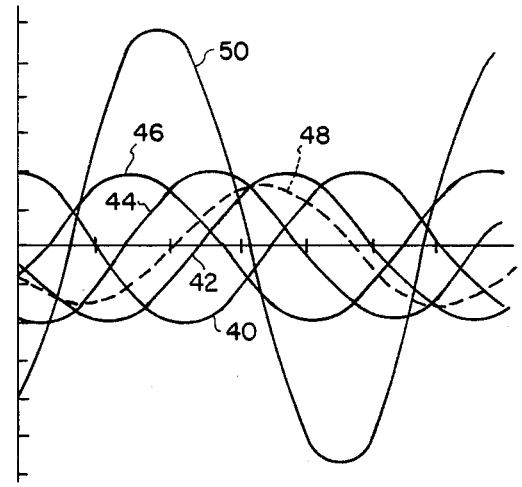

FIG. 2d shows the situation when the object is located at approximately 60 millimeters from the transducer and the curves 42, 44, 46, and 48 are considerably out of phase. The magnitude of the summation curve 48 has now decreased below the level of the individual curves while the relative curve 50 representing the use of the present invention is about twice as large as curve 48.

Figure 2E:
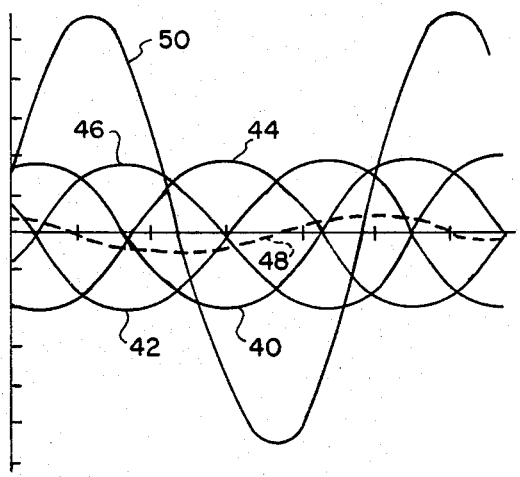

In FIG. 2e, the situation is represented when the object is at approximately 50 millimeters from the transducer and it is seen that the individual curves 42, 44, and 46 are almost totally out of phase with one another so that the effect is subtractive rather than additive. As a result, curve 48 representing the total of the curves is now only slightly above and below the zero level. It will be recalled that a first null or zero signal occurs when an object is located at 47.79 millimeters from the transducer in the mathematical analysis above. It should also be noted that the curve 50 representing the relative magnitude of the signal when the present invention is employed is several time larger than that of the signal represented by curve 48.

Figure 2F:
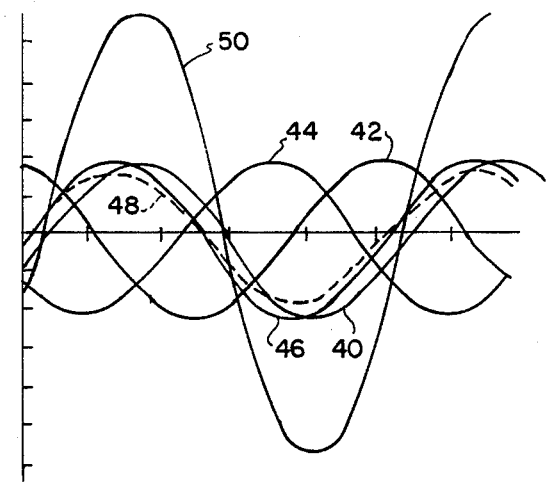

FIG. 2f shows the situation at a distance of 40 millimeters from the transducer head and it can be seen that curves 40 and 46 are coming close together and are almost in phase while curves 42 and 44 remain somewhat out of phase with respect to the other two. As a result, the summation curve 48 is now larger than was the case in FIG. 2e although it is in the opposite sense. In other words, the signal would have passed from possitive through zero to negative in going from FIG. 2e to FIG. 2f. In actual practice, however, the output signals are normally rectified so that the end signal is always positive. Again, however, it is seen that the curve 50 representing the signal utilizing the present invention is significantly larger than the summation curve 48.

Figure 3:
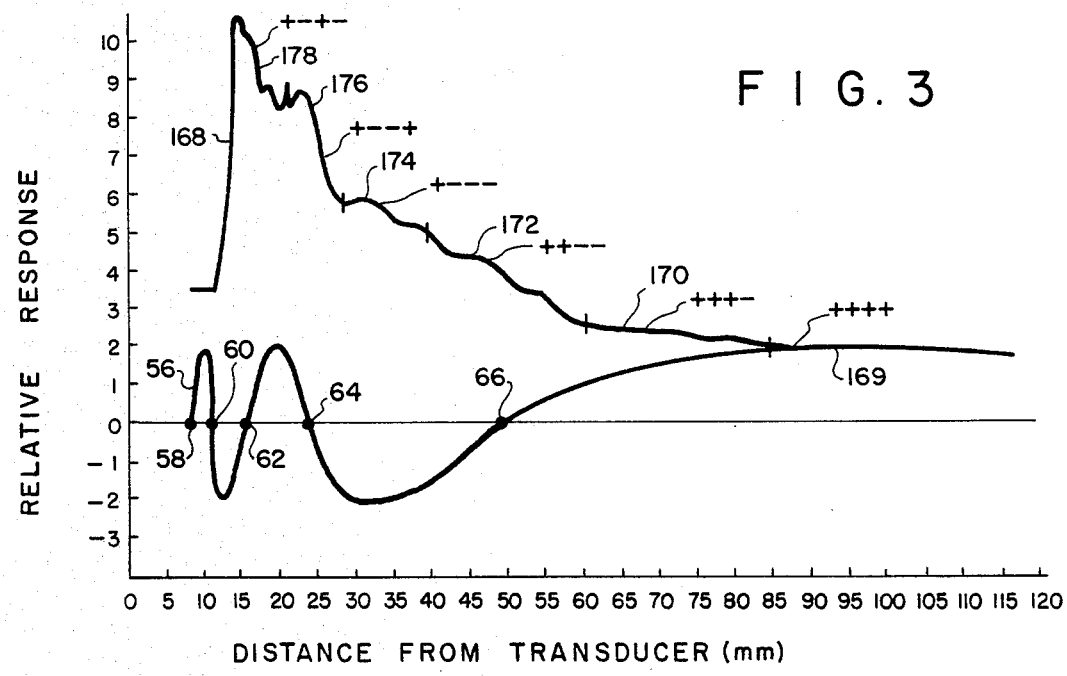
FIG. 3 is a graph showing the theoretical relative response between a non-compensated transducer and the transducer of the present invention at various distances from the transducer.

Referring now to FIG. 3, a curve 56 is shown representing the summation output of an uncompensated transducer with objects at various distances from the transducer head. It is seen that zero cross-overs occur at points represented by reference numerals 58, 60, 62, 64, and 66. Point 58 is located at a distance approximately 8.50 millimeters from the transducer head; point 60 is located at a distance approximately 11.12 millimeters from the transducer head; point 62 is located a distance approximately 15.34 millimeters from the transducer head; point 64 is located a distance approximately 23.57 millimeters from the transducer head; and point 66 is located a distance approximately 47.79 millimeters from the transducer head. Curve 56 can be drawn by looking at the placement of the individual curves 40, 42, 44, and 46 such as shown in FIGS. 2a through 2f for all positions of the remote object from a distance starting at about 8 millimeters on up to a distance up to of about 150 millimeters. As mentioned above, those portions of the curve which extend below the zero line in FIG. 3 would, in actual practice, be rectified so that they were above the zero axis and that all resultant signals would be positive. It is seen from FIG. 3 that there are several locations along the axis of the transducer where reflections will cancel each other out and thus the transducer will produce no output signal. To overcome this problem, the present invention utilizes a technique whereby the outputs of the various transducing elements 12, 14, 16, and 18 in FIG. 1 are subject to phase reversal at predetermined times representing predetermined distances for a reflecting object so that curves which might otherwise tend to cancel one another become additive.

Referring back again to FIG. 1, the output of transducer element 12 is shown connected by conductor 70 to a differential amplifier 72 having its other input connected to signal ground as at 74. Differential amplifier 72 has a first output 76 which will have a signal in phase with the signal on line 70 and a second output 78 which will have a signal 180 degrees out of phase with the signal on line 70. In similar fashion, transducer element 14 is shown connected by a conductor 80 to a second differential amplifier 82 having its other input connected to signal ground as at 84. The in-phase output of differential amplifier 82 is shown on a line 86 and the out-of-phase output of differential amplifier 82 is shown on line 88. Likewise, transducer element 16 is shown connected by a conductor 90 to a third differential amplifier 92 having its other input connected to ground as at 94. The in-phase output of differential amplifier 92 is shown on a line 96 while the out-of-phase output of differential amplifier 92 is shown on an output line 98. Finally, the central transducing element 18 is shown connected by a conductor 100 to a fourth differential amplifier 102 having its other input connected to signal ground as at 104. The in-phase output of differential amplifier 102 is shown on a line 106 and the out-of-phase signal from differential amplifier 102 is shown on a line 108.

Line 76 is connected to a switch 110, line 78 is connected to a switch 112, line 86 is connected to a switch 114, line 88 is connected to a switch 116, line 96 is connected to a switch 118, line 98 is connected to a switch 120, line 106 is connected to a switch 122, and line 108 is connected to a switch 124. The output of switches 110-124 are shown connected by lines 130, 132, 134, 136, 138, 140, 142, and 144 respectively to a summation device 146 having a summed output shown as an arrow 148. Switches 110-124 are turned off and on by a timer and logic circuit shown as box 150 having an output to switch 110 on a line 152, to switch 122 by line 154, to switch 114 by a line 156, to switch 116, by a line 158, to a switch 118 by a line 160, to switch 120 by a line 162 to switch 122 by a line 164 and to switch 124 by a line 166. While switches 110 and 112, 114 and 116, 118 and 120 and 122 and 124 have been shown as separate switches, each pair may comprise a single pole double throw switch with its switch arm connected to summation device 146 and its two contacts connected to the two outputs for its corresponding amplifier 72, 82, 92, and 102 respectively. The outputs from the logic and timer circuit would then operate the switch arms from one contact to another at the required times.

The timer and logic circuit 150 may comprise a standard ultrasonic pulse generator which transmits a pulse to the elements 12-18 over a line 167 and simultaneously starts a timer which is preset to produce signals to switches 110-124 at predetermined times representing predetermined distances for the sonic pulses from elements to objects in the body under examination. By knowing the velocity of sound in a body to be approximately 1540 meters per second, the distance to an object in the body can be determined. Thus, the timer will be set to turn the switches 110-124 on and off at appropriate object distances. For example, by observing graphs similar to those seen in FIGS. 2a through 2f, it can be determined that beyond distances of about 85 or so millimeters from the transducer the individual signals 40-46 are sufficiently in phase with one another that no compensation is deemed necessary. Accordingly, the timer and logic circuit 150 would operate to cause switches 110, 114, 118, and 122 to be on and switches 112, 116, 120, and 124 to be off, and thereby permit only the in-phase components of the signals from differential amplifiers 72, 82, 92, and 102 to be presented to the summation circuit 146. The output 148 in FIG. 1 will therefore be approximately what it would be without the present invention as is seen by curve 50 in FIG. 2a. By further analysis of the individual curves at all of the various distances a determination can be made as to when certain of the switches should be activated so as to phase reverse one or more of the outputs of transducer elements 12-18 to obtain the best summation output on line 148. The output 148 from summation circuitry 146 for the theoretical transducer used in connection with FIGS. 2a-2f is shown in FIG. 3 as curve 168.

A first portion of curve 168, shown by reference numeral 169, extends from the far right to about 85 millimeters in FIG. 3. This section 169 of curve 168 is shown with four plus signs "++++" indicating that in this portion of the curve the in-phase components of the outputs of transducers 12, 14, 16, and 18 of FIG. 1 are passed to the summation circuitry 146. It is also seen that portion 169 of curve 168 is the same as the far right hand portion of curve 56 representing the situation which occurs without the present invention.

At approximately 85 millimeters in FIG. 3, the four curves 40, 42, 44, and 46 of FIGS. 2a-2f have moved sufficiently apart that the magnitude of the summation signal without the present invention begins to decay. It can be determined that from about 85 millimeters to about 60 millimeters the summation signal will be enhanced if the outer element 12 of FIG. 1 is phase reversed. This portion of curve 168 is shown in FIG. 3 as portion 170 and the condition of the transducer elements is shown as "+++−" indicating that switches 122, 118, and 114 are on thereby passing the in-phase components from transducer elements 18, 16, and 14 but the timer and logic circuit 150 has turned switch 110 off and now has turned switch 112 on thereby passing the out-of-phase component of the signal from transducer element 12. The result of the switching can be seen in FIG. 2b where the curve 50 is somewhat higher than the curve 48 and can be seen in FIG. 3 where line segment 170 becomes progressively larger than its counterpart on curve 56 for distances from about 85 millimeters to about 60 millimeters.

Again, by analyzing the curves such as those shown in FIGS. 2a through 2f, it can be determined that the signal can be further enhanced in an area between about 60 millimeters and about 40 millimeters by phase reversing the output signals from both transducers 12 and 14. This segment of curve 168 is shown by reference numeral 172 and indicating that this portion of the curve is "++--". Curve portion 168 is seen to be significantly higher than its counterpart on curve 56 because, as seen from curves such as shown in FIG. 2e, by phase reversing two of the signals 40 and 42 with respect to signals 44 and 46 an additive rather than a subtractive effect occurs. Accordingly, between about 60 millimeters and about 40 millimeters the timer and logic circuitry 150 will turn switches 112 and 116 on while turning switches 110 and 114 off and leaving switches 120 and 124 on.

In similar fashion from about 40 millimeters to about 28 millimeters it has been found desirable to phase reverse the outputs from transducer elements 12, 14, and 16 as is shown in FIG. 3 by the portion of curve 168 having reference numeral 174 and the indication "+---". It is seen in this area 168 that the transducers 12, 14, and 16 are phase reversed thus producing an output considerably higher than the output represented by the counterpart on line 56. This phase reversal is performed by the timer and logic circuit 150 turning switches 112, 116, and 120 on, switches 110, 114, and 118 off and leaving switch 124 on thereby passing phased reversed signals along lines 132, 136, and 140 but in-phase signals on line 142 to summation circuit 146.

In similar fashion between about 28 millimeters and about 20 millimeters it can be determined that the best combination is to allow the transducer 12 and transducer 18 to pass in-phase signals but to phase reverse the signals from transducers 14 and 16. This is shown in FIG. 3 by the portion of the curve 168 given reference numeral 176 and the designation "+--+". In this event, the timer and logic circuit 150 will turn switches 110, 116, 120, and 122 on while turning switches 112, 114, 118, and 124 off thereby passing in-phase signals on lines 130 and 142 and phased reverse signals on lines 136 and 140 to the summation circuit 146. Finally, it can be determined that below about 20 millimeters from the transducer the best arrangement is to have transducer elements 12 and 16 produce in-phase signals while transducer elements 14 and 18 produce phase reversed signals. This is shown in FIG. 3 by the portion of curve 168 given reference numeral 178 and a designation "+-+-" which, it is seen, is far greater than its counterpart on curve 56. In FIG. 1 this configuration is made possible by the timer and logic circuit causing switches 110, 116, 118, and 124 to be on while switches 112, 114, 120, and 122 are off thereby passing in-phase signals on lines 130 and 138 and phase reverse signals on lines 132 and 144 to the summation circuit 146.

The values shown in FIG. 3 were obtained from a theoretical analysis of the theoretical wave shapes and phasing shown in FIGS. 2a-2f. In actual measurements taken from an annular non-focused transducer operating at 3.5 MHz, the graph of FIG. 4 was obtained.

Figure 4:
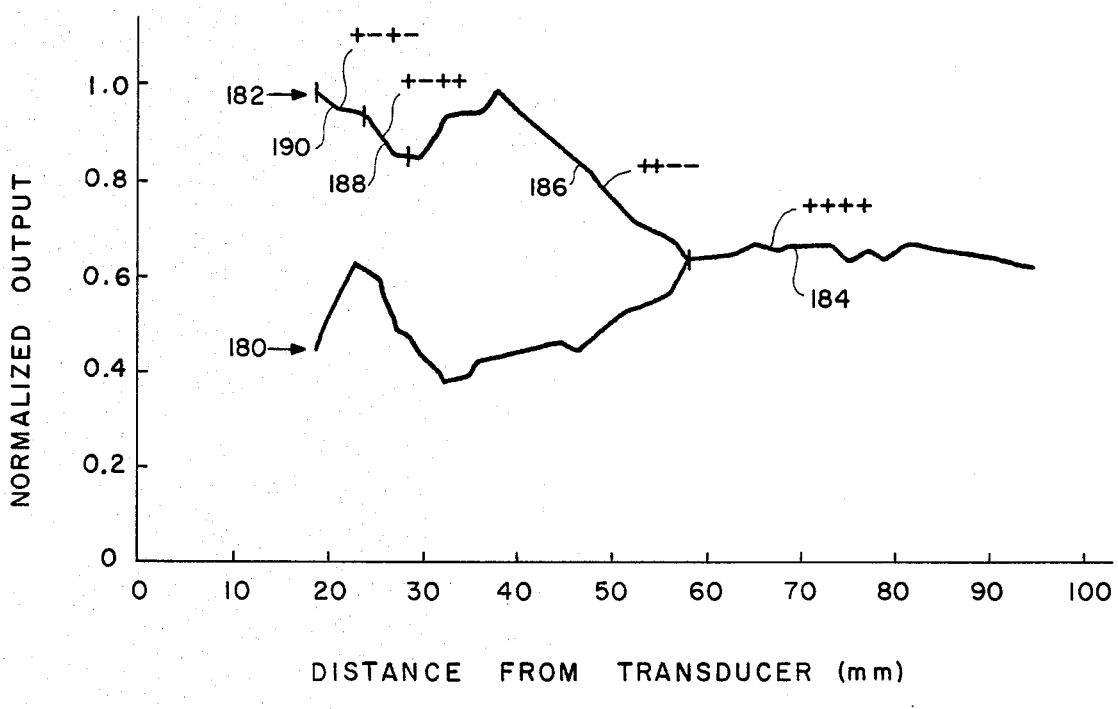
FIG. 4 is a graph like FIG. 3 showing actual values obtained from one transducer.

In FIG. 4, the amplitude of the maximum output signal was normalized at a value of 1.0 and all other signals were measured as a fraction thereof. In FIG. 4, a curve 180 represents the variation of output without the present invention and a curve 182 represents the variation of output utilizing the present invention. As can be seen in FIG. 4, from a distance of about 95 millimeters to about 60 millimeters from the transducer, there was no appreciable advantage in switching the phasing of any of the elements. This is seen in FIG. 4 as the portion 184 having "++++" phasing. From about 60 millimeters to about 30 millimeters in a portion of the curve identified as 186, curve 182 increases dramatically from curve 80. It was found that a "++--" phasing produced the best results, i.e., with switches 110 and 114 passing in-phase signals from transducer elements 12 and 14 and switches 120 and 124 passing the out-of-phase signals from elements 16 and 20. This represents a difference from the theoretical phasing found in FIG. 3 wherein a "+++-" phasing was used as the first phasing relationship after the common "++++" phasing. In the actual measurements taken with the transducer of FIG. 4, however, it was found that the "+++-" phasing did not produce a significant benefit and accordingly this phasing was omitted.

From about 30 millimeters to about 25 millimeters from the transducer in a portion 188 of curve 180 a phase relationship of "+-++" was found best, i.e., with switches 110, 118, and 122 passing in-phase signals from elements 12, 16, and 18, and switch 158 passing an out-of-phase signal from element 14 in FIG. 1. This also represents a variation from the theoretical calculations of FIG. 3 where a "+-++" phasing was not used at all. In actual practice it was found, however, that the "+-++" phasing produced the best result and accordingly it was used with this particular transducer.

From a point about 25 millimeters to about 20 millimeters from the transducer in a portion 190 of curve 180, a phase relationship "+-+-" was found best, i.e., with switches 110 and 118 passing in-phase signals from elements 12 and 16, and switches 116 and 124 passing out-of-phase signals from elements 14 and 18 of FIG. 1. This is in agreement with the theoretical phasing of the portion 178 of curve 168 in FIG. 3. It is thus seen that by selectively turning on switches 110-124 the in-phase or out-of-phase signals from transducing elements 12, 14, 16, and 18 can be performed in such a manner as to increase the relative magnitude of the summed output to values well above those which would be obtained with straight summation of the signals from the transducing elements.

In addition to the advantage of obtaining an enhanced output signal magnitude, the present invention also operates to provide a signal with a much narrower beam width than was previously possible.

Figure 5:
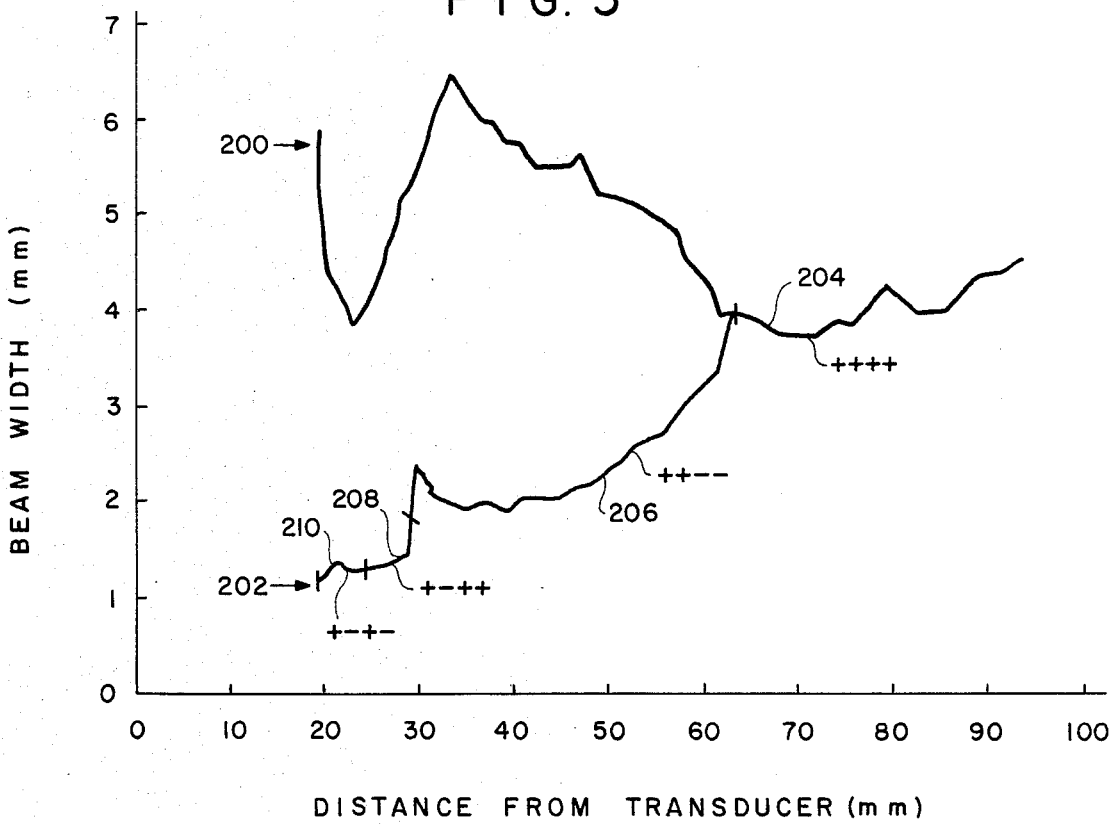
FIG. 5 is a graph showing beam width variation using the transducer used in FIG. 4.

FIG. 5 shows a graph of the beam width versus the distance from the transducer for the same transducing elements and substantially the same phasings as was used in connection with FIG. 4. The upper curve identified by reference numeral 200 in FIG. 5 represents the beam width variations when the present invention is not used while the lower curve 202 represents the beam width variation when the present invention is employed. It will be noted that from about 65 millimeters on out to the right in FIG. 5 in a portion of the curve identified by reference numeral 204 the phasing was "++++" as was in the case in FIG. 4 although in FIG. 4 the "++++" started at about 60 millimeters. The difference arose because while there was little difference between the magnitude of the signals with or without the present invention beyond 60 millimeters in FIG. 4, when examining beam width it was found that at 60 millimeters the transducer being tested showed a considerable advantage using the present invention. However, above 65 millimeters the beam width shown by both curves is substantially the same. Accordingly, if this particular transducer were put into medical use, the timing and logic circuit 150 of FIG. 1 would probably be set to switch amplifier outputs 78 and 88 into the summer circuit 146 and block amplifier outputs 76 and 86.

From about 65 millimeters down to around 30 millimeters in a portion of the curve identified by reference numeral 206 the phasing is "+ + − −" as was the case in FIG. 4 and it is seen that the beam width drops off significantly from its counterpart on curve 200. From about 30 millimeters to about 25 millimeters in a portion of the curve identified by reference numeral 208 the phasing is "+ − + +" as was the case in connection with FIG. 4 and the beam width drops off again significantly from what it would have been without the invention as shown by curve 200. Finally, in the area from about 25 millimeters down to about 20 millimeters in a portion of the curve identified by reference numeral 210 the phasing is "+ − + −" as it was in FIG. 4 and again the beam width is significantly narrower than it would have been if the invention were not employed. Clearly the beam width with the present invention is much narrower than a transducer beam width without the present invention throughout the range where the present invention is employed. Of course, with different transducers there might be different phase relationships at various points to produce the optimum results. Experimentation in measuring the amplitude and beam width from an actual transducer at various distances therefrom will enable one skilled in the art to determine the best phase relationships and switching points to use.

Many changes and mmodifications to the apparatus shown in connection with the preferred embodiments of the present invention will occur to those skilled in the art. For example, wherever in-phase and out-of-phase components are shown, the exact reverse could be employed since that would merely change the sign of the result and the rectified signal would produce the same advantage. Furthermore, the specific phasings mentioned in connection with the preferred embodiment were picked in accordance with experimentation and depending upon the transducer used, and the medium it is employed in, other type phasing may be found to be more desirable. Also a number of other timer and logic circuits will occur to those skilled in the art. I therefore do not wish to be limited by the disclosures used in connection with the description of the preferred embodiments, but intend only to be limited by the following claims.

I claim:

1. Apparatus for use with a transducer having first and second portions each of which produce an electrical signal that varies on opposite sides of a reference potential upon receipt of a signal from a remote object, the first and second portions receiving a signal from the remote object at times which differ by an amount dependent on the distance to the remote object with the result that at certain distances from the remote object, the electrical signal from the first portion may be predominantly on the opposite side of the reference potential from the electrical signal from the second portion, comprising:

modifying means connected to the first and second portions to receive the electrical signals therefrom, said modifying means operable to produce first and second pairs of resultant signals which vary with the electrical signals from said first and second portions, respectively, each of which pairs of resultant signals includes first and second resultant signals varying in opposite sense to each other;

range finding means for determining the distance to the remote object and producing an output signal when the object is nearer than a predetermined distance; and switch means connected to said modifying means to receive the resultant signals therefrom and connected to said range finding means to receive the output signal therefrom, said switch means operable for object distances greater than the predetermined distance to pass the first and block the second resultant signal of each pair of resultant signals and upon receipt of an output signal from said range finding means to pass the second and block the first of the resultant signals in the first resultant signal pair and to pass the first and block the second of the resultant signals in the second resultant signal pair.

2. Apparatus according to claim 1 wherein the transducer is an ultrasonic transducer, said transducer including means for transmitting an ultrasonic signal to the remote object and means for receiving a reflected ultrasonic signal from the remote object, and wherein the first and second portions are ultrasonic receiving elements spaced apart from one another.

3. Apparatus according to claim 2 where the range finding means comprises a timer which measures the time from the transmitting of the ultrasonic signal to the receipt of the reflected signal.

4. Apparatus according to claim 3 wherein the predetermined distance is chosen so that the second of the resultant signals in the first resultant signal pair added to the first resultant signal in the second resultant signal pair is larger than the sum of the first resultant signals in said first and second resultant signal pairs for distances nearer than the predetermined distance.

5. Apparatus according to claim 4 wherein the modifying means comprises first and second differential amplifiers.

6. Apparatus according to claim 1 further including summing means connected to said switch means to receive the passed signals and to produce a summed signal indicative of their combined value.

7. Apparatus according to claim 4 further including summing means connected to said switch means to receive the passed signals and to produce a summed signal indicative of their combined value.

8. Apparatus according to claim 2 wherein the first and second portions are parts of an annular array.

9. Apparatus for enhancing the summed output of a plurality of ultrasonic transducing elements spaced apart from each other, each element operable upon receipt of an ultrasonic signal from a remote object to produce an electrical signal which varies on either side of a reference potential, the electrical signals from the transducing elements being relatively phased by an amount which depends upon the distance to the object so that when the object is proximate at least one predetermined distance, the electrical signals interfere with one another so as to produce a null value when summed, comprising:

converting means connected to the plurality of transducing elements and operable to respond to each electrical signal to convert it into two resultant signals a first of which is in phase and the second of which is out-of-phase with the electrical signal it is responsive to;

range determination means operable to sense the distance to the object and to produce an output signal when the object is proximate at least one predetermined distance;

switch means connected to said converting means to receive the resultant signals and connected to said range finding means to receive the output signal, said switch means in a first condition passing the first and blocking the second resultant signal of each resultant signal pair and in a second condition, upon receipt of the output signal, passing the second and blocking the first resultant signal of at least one of the resultant signal pairs so as to prevent a null value of the passed signals when summed.

10. Apparatus according to claim 9 wherein the range determination means is a timer to measure the time for travel of the ultrasonic signal from the remote object.

11. Apparatus according to claim 10 further including means for energizing said transducing elements in order to produce an ultrasonic signal, wherein said transducing elements are operable to receive a reflection of such signal from said remote object.

12. Apparatus according to claim 11 wherein the converting means comprises a plurality of differential amplifiers, one connected to each transducing element.

13. Apparatus according to claim 12 further including summing means connected to said switch means to receive the passed signals and sum them to produce a final signal.

14. Apparatus according to claim 13 wherein the transducing elements are arranged in annular fashion.

15. Apparatus for use with a transducer having first and second portions each of which produce an electrical signal that varies on opposite sides of a reference potential upon receipt of a signal from a remote object, the first and second portions receiving a signal from the remote object at times which differ by an amount dependent on the distance to the remote object with the result that at certain distances from the remote object, the electrical signal from the first portion may be predominantly on the opposite side of the reference potential from the electrical signal from the second portion, comprising:

range finding means for determining the distance to the remote object and producing an output signal when the object is nearer than a predetermined distance; and signal processing means connected to the first and second portions to receive the electrical signals therefrom and connected to said range finding means to receive the output signal therefrom, said signal processing means operable to produce first and second resultant signals which vary with the electrical signals from said first and second portions, respectively, said signal processing means including phase reversal means for selectively reversing the phases of said first and second resultant signals in response to the output signal from said range finding means.

16. Apparatus according to claim 15 wherein the transducer is an ultrasonic transducer, said transducer including means for transmitting an ultrasonic signal to the remote object and means for receiving a reflected ultrasonic signal from the remote object, and wherein the first and second portions are ultrasonic receiving elements spaced apart from one another.

17. Apparatus according to claim 16 wherein said range finding means comprises a timer which measures the time from the transmitting of the ultrasonic signal to the receipt of the reflected signal.

18. Apparatus according to claim 17 wherein the predetermined distance is chosen so that the sum of the first and second resultant signals is larger than the sum of the electrical signals from said first and second portions for distances nearer than the predetermined distance.

19. Apparatus according to claim 18 wherein said signal processing means comprises first and second differential amplifiers.

20. Apparatus according to claim 15 further including summing means connected to said signal processing means for adding the first and second resultant signals.

21. Apparatus according to claim 18 further including summing means connected to said signal processing means for adding the first and second resultant signals.

22. Apparatus according to claim 16 wherein the first and second portions are parts of an annular array.

* * * * *